United States Patent
Yoshida et al.

(10) Patent No.: US 10,696,563 B2
(45) Date of Patent: Jun. 30, 2020

(54) HEXAGONAL PLATE-SHAPED ZINC OXIDE PARTICLES, METHOD FOR PRODUCTION OF THE SAME, AND COSMETIC, FILLER, RESIN COMPOSITION, INFRARED REFLECTIVE MATERIAL, AND COATING COMPOSITION CONTAINING THE SAME

(71) Applicant: SAKAI CHEMICAL INDUSTRY CO., LTD., Sakai-shi, Osaka (JP)

(72) Inventors: Ryohei Yoshida, Iwaki (JP); Satoru Sueda, Iwaki (JP); Mitsuo Hashimoto, Iwaki (JP); Mizuho Wada, Sakai (JP)

(73) Assignee: SAKAI CHEMICAL INDUSTRY CO., LTD., Sakai-shi, Osaka (JP)

( * ) Notice: Subject to any disclaimer, the term of this patent is extended or adjusted under 35 U.S.C. 154(b) by 0 days.

(21) Appl. No.: 15/116,425

(22) PCT Filed: Dec. 16, 2014

(86) PCT No.: PCT/JP2014/083227
§ 371 (c)(1),
(2) Date: Aug. 3, 2016

(87) PCT Pub. No.: WO2015/118777
PCT Pub. Date: Aug. 13, 2015

(65) Prior Publication Data
US 2016/0347624 A1   Dec. 1, 2016

(30) Foreign Application Priority Data
Feb. 7, 2014   (JP) .................................. 2014-022360

(51) Int. Cl.
*C01G 9/02* (2006.01)
*A61K 8/27* (2006.01)
(Continued)

(52) U.S. Cl.
CPC .............. *C01G 9/02* (2013.01); *A61K 8/0245* (2013.01); *A61K 8/27* (2013.01); *A61Q 17/04* (2013.01);
(Continued)

(58) Field of Classification Search
CPC .......... C01G 9/02; A61K 8/27; A61K 8/0245; A61Q 17/04; C01D 7/1291; C08K 3/22; G02B 5/208; C09C 1/043
See application file for complete search history.

(56) References Cited

U.S. PATENT DOCUMENTS

| 5,976,511 | A | 11/1999 | Ohtsu et al. |
|---|---|---|---|
| 2007/0149395 | A1 | 6/2007 | Kroell et al. |

(Continued)

FOREIGN PATENT DOCUMENTS

| CA | 2837441 | 12/2012 |
|---|---|---|
| CN | 103492320 A | 1/2014 |

(Continued)

OTHER PUBLICATIONS

Cho et al., Synthesis of hierarchial hexagonal zinc oxide/zinc aluminum hydroxide heterostructures through epitaxial growth using microwave irradiation, 2009, CrystEngComm, 11, 1650-1657.*

(Continued)

*Primary Examiner* — James A Fiorito
(74) *Attorney, Agent, or Firm* — Hamre, Schumann, Mueller & Larson, P.C.

(57) ABSTRACT

It is one of objects of the present disclosure to provide hexagonal plate-shaped zinc oxide particles which can be used suitably for a cosmetic, a filler, a resin composition, an infrared radiation reflective material, and a coating composition, and a method for producing the same.

(Continued)

Hexagonal plate-shaped zinc oxide particles having a primary particle diameter of 1.1 μm or more and a D90/D10 of 3.0 or less in particle size distribution.

9 Claims, 7 Drawing Sheets

(51) Int. Cl.
    *A61Q 17/04*     (2006.01)
    *A61K 8/02*     (2006.01)
    *C09C 1/04*     (2006.01)
    *C09D 7/40*     (2018.01)
    *C08K 7/00*     (2006.01)
    *C08K 3/22*     (2006.01)
    *G02B 5/20*     (2006.01)

(52) U.S. Cl.
    CPC .................. *C08K 3/22* (2013.01); *C08K 7/00* (2013.01); *C09C 1/043* (2013.01); *C09D 7/70* (2018.01); *G02B 5/208* (2013.01); *A61K 2800/412* (2013.01); *C01P 2002/72* (2013.01); *C01P 2004/03* (2013.01); *C01P 2004/20* (2013.01); *C01P 2004/22* (2013.01); *C01P 2004/51* (2013.01); *C01P 2004/54* (2013.01); *C01P 2004/61* (2013.01); *C01P 2004/62* (2013.01); *C01P 2006/12* (2013.01); *C08K 2003/2296* (2013.01); *C08K 2201/003* (2013.01); *C08K 2201/005* (2013.01)

(56) References Cited

U.S. PATENT DOCUMENTS

| | | | |
|---|---|---|---|
| 2009/0087463 | A1 | 4/2009 | Yagyu et al. |
| 2013/0216834 | A1 | 8/2013 | Hashimoto et al. |
| 2014/0050925 | A1 | 2/2014 | Sueda et al. |
| 2015/0050496 | A1 | 2/2015 | Sueda |

FOREIGN PATENT DOCUMENTS

| | | |
|---|---|---|
| CN | 104159850 | 11/2014 |
| EP | 2759526 | 7/2014 |
| JP | 62275182 | 11/1987 |
| JP | 5222317 | 8/1993 |
| JP | 6345427 | 12/1994 |
| JP | 7-165422 | 6/1995 |
| JP | 2007161578 | 6/2007 |
| JP | 2008-266445 | 11/2008 |
| JP | 2010185133 | 8/2010 |
| JP | 5365763 | 9/2013 |
| JP | 2013-245139 | 12/2013 |
| WO | 2007/119395 | 10/2007 |
| WO | 2012/036082 | 3/2012 |
| WO | 2012/147886 | 11/2012 |
| WO | 2013/042596 | 3/2013 |
| WO | 2013035545 | 3/2013 |
| WO | 2013042596 | 3/2015 |

OTHER PUBLICATIONS

Partial Translation of Paragraph 23-26 of JP H7-165422A (Year: 1995).*
International Search Report issued for International Application No. PCT/JP2014/084115 dated Mar. 3, 2015 with English translation (3 pages).
Written Opinion issued for International Application No. PCT/JP2014/084115 dated Mar. 3, 2015 (4 pages).
International Search Report, May 19, 2015, PCT/JP2014/083227 with English translation (5 pages).
Notification of transmittal of translation of the international preliminary report on patentability, dated Aug. 18, 2016, International Application No. PCT/JP2014/083227 (8 pages).
Office Action; Tawain Patent Application No. 104100926, dated Sep. 10, 2018 (5 pages).

* cited by examiner

HEXAGONAL PLATE-SHAPED ZINC OXIDE PARTICLES, METHOD FOR PRODUCTION OF THE SAME, AND COSMETIC, FILLER, RESIN COMPOSITION, INFRARED REFLECTIVE MATERIAL, AND COATING COMPOSITION CONTAINING THE SAME

TECHNICAL FIELD

The present disclosure relates to hexagonal plate-shaped zinc oxide particles, a method for producing the same, and a cosmetic, a filler, a resin composition, an infrared radiation reflective material and a coating composition containing the same.

BACKGROUND OF THE DISCLOSURE

As for makeup cosmetics such as a foundation, a feeling in use is considered important, and an ultraviolet shielding property is required in recent years. An ultraviolet shielding material is required to be blended for improving the ultraviolet shielding property. However, zinc oxide microfine particles and titanium oxide microfine particles widely used for a sunscreen agent are inferior in slippage, so that these particles inhibit a good feeling in use. Therefore, an ultraviolet shielding material which can provide an excellent feeing in use has been required.

Further, the zinc oxide particles are used as an inorganic filler contained in a resin composition and a coating. The use of the inorganic filler may include a heat releasing filler utilizing the high thermal conductivity of the zinc oxide particles, a filler for ultraviolet shielding or infrared radiation reflection, and so on.

Furthermore, zinc oxide particles have attracted the attention as inorganic particles having an infrared radiation reflective property, in recent years. The temperature of various products raises when the products absorb infrared radiation. Therefore, for energy saving, a heat insulating coating has been prepared by blending an inorganic pigments which can reflect or shield infrared radiation so that the temperature raising of various products and buildings may be suppressed by using the heat insulating coating.

Zinc oxide particles have an infrared radiation reflective performance. The pattern of absorption wavelength varies depending on the particle shape or particle size. Therefore, if the absorption wavelength in an infrared region is enhanced, an absorption region extends to a visible light region so that a coloring is caused. In the heat insulating coating, the coloring of the pigments for heat insulating is not preferred because the color tone of the obtained coating is influenced.

Patent document 1 discloses hexagonal plate-shaped zinc oxide particles having a controlled particle shape. Hexagonal plate-shaped zinc oxide particles having a particle diameter of 0.5 µm or more are suitably used as particles in foundation applications because very good slippage and excellent feeling in use are provided. However, when the hexagonal plate-shaped zinc oxide particles having an average particle diameter of 0.5 to 1.0 µm disclosed in patent document 1 are used, the slippage is not so bad as the conventional zinc oxide microfine particles but the feeling in use is insufficiently as a material compounded in the current makeup cosmetics. Therefore, it is required to obtain hexagonal plate-shaped zinc oxide particles having a larger particle diameter and a uniform particle size.

Patent Document 2 discloses hexagonal plate-shaped zinc oxide particles having a multilayer structure and having a particle diameter of 10 µm. However, when the zinc oxide particles are compounded in a cosmetic, sufficient good performances in a slippage and so on may not be provided.

Patent Document 3 discloses zinc oxide particles having an average particle diameter of 3 to 20 µm, and an infrared radiation reflective performance and a slippage. However, the particle shape is not disclosed and the obtained particles are indefinite-shaped zinc oxide particles. Such zinc oxide particles cannot exhibit sufficient good performances, for example, the infrared radiation reflective performance and the slippage when used in a cosmetic.

PRIOR TECHNICAL DOCUMENTS

Patent Documents

[Patent Document 1] WO 2012/147886
[Patent Document 2] Japanese Kokai Publication 2013-245139
[Patent Document 3] WO 2012/036082

SUMMARY OF INVENTION

Problems to be Solved by the Invention

It is one of objects of the present disclosure to provide hexagonal plate-shaped zinc oxide particles which can be used suitably for cosmetics such as makeup cosmetics, and a method for producing the same. Further, another object is to provide hexagonal plate-shaped zinc oxide particles which can be used as an infrared radiation reflective agent without coloring.

Means for Solving Object

The present disclosure relates to hexagonal plate-shaped zinc oxide particles having a primary particle diameter of 1.1 µm or more and a D90/D10 of 3.0 or less in particle size distribution.

The hexagonal plate-shaped zinc oxide particles preferably have a MIU (average friction coefficient) of 0.87 or less and a MMD (mean deviation of friction coefficient) of 0.035 or less.

The present disclosure relates to a method for producing the hexagonal plate-shaped zinc oxide particles, comprising a step (1) of preparing a water slurry of raw zinc oxide having a pH of 10 or more, a step (2) of mixing the slurry prepared in said step (1) and a zinc salt aqueous solution at 35° C. or less, and a step (3) of aging the mixed slurry with heating.

The present disclosure relates to a cosmetic containing the hexagonal plate-shaped zinc oxide particles mentioned above.

The present disclosure relates to a filler comprising the hexagonal plate-shaped zinc oxide particles mentioned above.

The present disclosure relates to a resin composition containing the hexagonal plate-shaped zinc oxide particles mentioned above.

The present disclosure relates to an infrared radiation reflective material comprising the hexagonal plate-shaped zinc oxide particles mentioned above.

The present disclosure relates to a coating composition containing the hexagonal plate-shaped zinc oxide particles mentioned above.

Effects of the Invention

The hexagonal plate-shaped zinc oxide particles of the present disclosure can be suitably used for makeup cosmetics as an ultraviolet shielding material when used in cosmetics. In addition, when used as a filler, excellent heat releasing performance and infrared radiation reflective ability may be achieved.

DETAILED DESCRIPTION OF PREFERRED EMBODIMENTS

Figure 1:
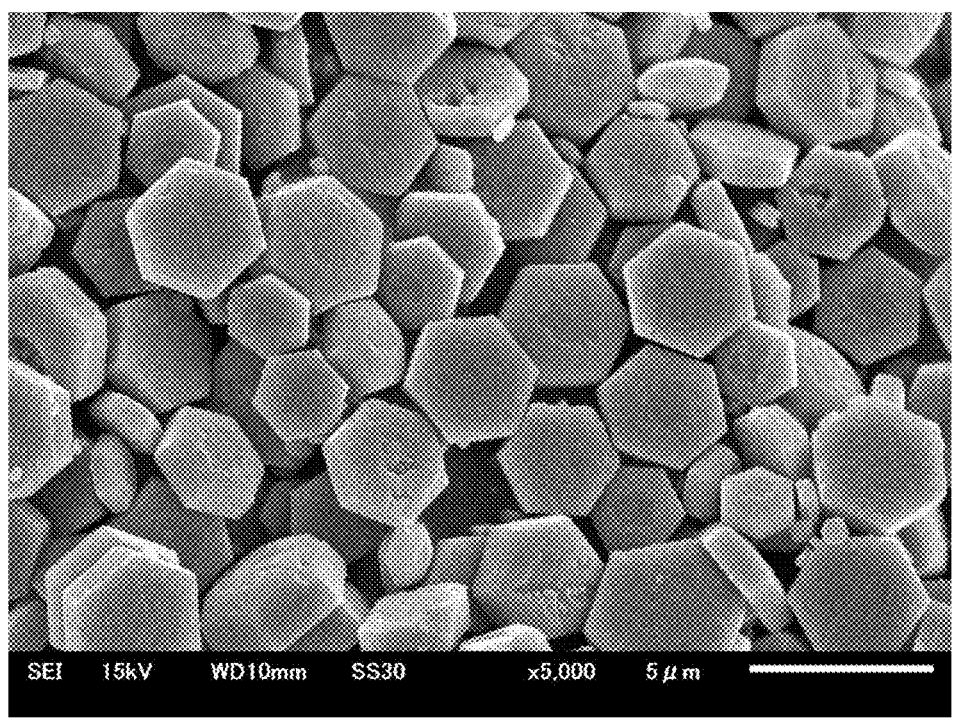
FIG. 1 is a scanning electron microscope photograph of zinc oxide particles of the present disclosure obtained in Example 1.

The hexagonal plate-shaped zinc oxide particles of the present disclosure have a hexagonal plate shape, a primary particle diameter of 1.1 μm or more and a sharp particle size distribution, so that the particles may be suitably used as an ingredient for cosmetics such as makeup cosmetics or a filler.

The hexagonal plate-shaped zinc oxide particles can be suitably used as a filler because the particle shape thereof is uniform so that the particles can be compounded in a matrix component at a high concentration. When used as a filler, the particles may be used as a heat releasing filler utilizing a high heat conductivity of zinc oxide particle, and may be used as an infrared radiation reflective filler. The hexagonal plate-shaped zinc oxide particles of the present disclosure may be suitably used as an infrared radiation reflective filler compounded in a heat insulating coating because the particles have better infrared radiation reflective ability than conventional zinc oxide particles and have a good transparency.

The hexagonal plate-shaped zinc oxide particles of the present disclosure have a D90/D10 of 3.0 or less. The particle size distribution broadens as the D90/D10 becomes larger, while the particle size distribution sharpens as the D90/D10 becomes smaller.

The values of D10 and D90 are obtained by measuring the distribution of particle diameter. D10 denotes a 10% cumulative particle diameter on the volume basis, and D90 denotes a 90% cumulative particle diameter on the volume basis. The D90/D10 is more preferably 2.8 or less. The hexagonal plate-shaped zinc oxide particles having a D90/D10 of 3.0 or less achieve an excellent powder touch when compounded in cosmetics and applied on the skin because the particle size thereof is uniform and an amount of microfine particles and coarse particles which inhibit a good feeling is small. In the present disclosure, the value of D90 and D10 is measured by the method described in the example.

The primary particle diameter of the hexagonal plate-shaped zinc oxide particles of the present disclosure is 1.1 μm or more. The primary particle diameter is more preferably 1.3 μm or more, still more preferably 2.0 μm or more. The upper limit of the primary particle diameter is not particularly limited but preferably 50 μm or less, more preferably 30 μm or less. The particles having a primary particle diameter of 1.1 μm or more show a good powder touch when used as a cosmetic ingredient. The primary particle diameter in the present disclosure is measured by the method described in the example.

The hexagonal plate-shaped zinc oxide particles of the present disclosure preferably have a MIU (average friction coefficient) of 0.87 or less. As the value of MIU (average friction coefficient) becomes smaller, the slippage of the obtained particles is good and the particle is slippery. If the hexagonal plate-shaped zinc oxide particles having a MIU (average friction coefficient) of more than 0.87 are compounded in cosmetics, the slippage may be reduced. Further, the hexagonal plate-shaped zinc oxide particles of the present disclosure preferably have a MMD (mean deviation of friction coefficient) of 0.035 or less. As the value of MMD (mean deviation of friction coefficient) becomes smaller, the roughness of the obtained particle is less and the particle is very smooth. If the hexagonal plate-shaped zinc oxide particles having a MMD (mean deviation of friction coefficient) of more than 0.035 are compounded in cosmetics, the feeling in use of the cosmetics may be inferior because a roughness increases. The MIU (average friction coefficient) is more preferably 0.85 or less and the MMD (mean deviation of friction coefficient) is more preferably 0.03 or less. In the specification, the MIU (average friction coefficient) and the MMD (mean deviation of friction coefficient) are measured by the methods described in detail in the example.

Further, the hexagonal plate-shaped zinc oxide particles of the present disclosure preferably have an aspect ratio of 2.5 or more. That is, the hexagonal plate-shaped zinc oxide particles having a hexagonal plate shape within the above-mentioned aspect ratio are preferred. When the particles are used especially for a cosmetic, good slippage and excellent feeling in use can be achieved owing to the above-mentioned shape. The aspect ratio is more preferably 2.7 or more, still more preferably 3.0 or more. In the specification, the aspect ratio is measured by the method described in the example.

In the present disclosure, Dmin/Dmax is preferably 0.3 or more. Dmax means a length of the largest diagonal line of three diagonal lines of the hexagonal-shaped surface of the hexagonal plate-shaped zinc oxide particle and Dmin means a length of the smallest diagonal line of three diagonal lines of the hexagonal-shaped surface of the hexagonal plate-shaped zinc oxide particle. Where Dmax is a length of a diagonal line of a regular hexagon, Dmin/Dmax denotes a deviation from the length of the diagonal line of the regular hexagon, and the deviation decreases as the value becomes closer to 1, while the deviation increases as the value becomes closer to 0. Dmin/Dmax is more preferably 0.5 or more, still more preferably 0.7 or more. In the present disclosure, Dmin/Dmax is measured by the method described in the example.

The hexagonal plate-shaped zinc oxide particles of the present disclosure preferably have a BET specific surface area of 1.9 $m^2/g$ or less. By adjusting the BET specific surface area within the above-mentioned range, the particles preferably have a good powder touch because the particle diameter thereof is large and an amount of microfine particles is small. In the present disclosure, the BET specific surface area is measured by the method described in the example.

The hexagonal plate-shaped zinc oxide particles of the present disclosure preferably have a spectral reflectance of 10% or more measured at 1000 nm, and 8% or more measured at 2000 nm. Especially when the particles are used for the heat insulating coating as mentioned above, it is preferred to show a high infrared radiation reflective ability. The spectral reflectance is measured by the method described in the example.

The hexagonal plate-shaped zinc oxide particles of the present disclosure preferably have a parallel light transmittance of 30% or more measured at 400 nm. If the parallel light transmittance is less than 30%, it is not preferred that the color tone of a cosmetic and a coating may be changed because the zinc oxide particles are colored. The parallel light transmittance at 400 nm is used as an indicator because the parallel light transmittance at 400 nm most closely reflects the actual apparent transmittance in a visible light region. The parallel light transmittance is measured by the method described in the example.

The hexagonal plate-shaped zinc oxide particles of the present disclosure have an excellent infrared radiation reflective ability, on the other hand, have a characteristic that the shielding ability in a visible light region is a little. Therefore, a coating film having a superior transparency may be obtained and the color tone of the obtained coating film is preferably not affected when the particles are used for purposes such as a cosmetic and a heat insulating coating, for which the color tone is important.

A method for producing the hexagonal plate-shaped zinc oxide particle having the above-mentioned shape is not particularly limited but may include a production method comprising a step (1) of preparing a water slurry of raw zinc oxide having a pH of 10 or more, a step (2) of mixing the slurry obtained in the step (1) with a zinc salt aqueous solution at 35° C. or less, and a step (3) of aging the mixed slurry with heating. The production method will be described below in detail.

The step (1) comprises preparing a water slurry of raw zinc oxide having a pH of 10 or more. By this step, the dispersibility of the raw zinc oxide into water is improved and the reactivity between the raw zinc oxide and the zinc salt aqueous solution is raised so that the particle diameter and the particle size distribution thereof may be controlled.

The raw zinc oxide used in the water slurry of raw zinc oxide is not particularly limited, but the particle diameter thereof is preferably 0.005 μm or more and 0.2 μm or less. The particle diameter of the raw zinc oxide corresponds to a diameter of a sphere having the same surface area as a specific surface area determined by a BET method. That is, the particle diameter is a value determined by the following calculation formula from a specific surface area: Sg determined by making a measurement using a fully automatic BET specific surface area measuring device Macsorb Model HM-1200 (manufactured by Mountech Co., Ltd.), and a true specific gravity of zinc oxide: ρ.

particle diameter(μm)=[6/($Sg \times \rho$)]

(Sg ($m^2/g$): specific surface area, ρ ($g/cm^3$): true specific gravity of particle)

As the true specific gravity of particle: ρ, a value of the true specific gravity of zinc oxide, i.e. 5.6, was used for the above calculation.

The raw zinc oxide is not particularly limited, and zinc oxide produced by a known method can be used. Examples of those that are commercially available may include FINEX-75, FINEX-50, FINEX-30, SF-15, and Fine Zinc Oxide manufactured by Sakai Chemical Industry Co., Ltd.

In the slurry of raw zinc oxide, the concentration of raw zinc oxide is preferably 10 to 500 g/l based on the total amount of the slurry.

A method for preparing the slurry is not particularly limited, and for example, may include a method of adding the raw zinc oxide to water and adjusting the pH at 10 or more by adding an alkaline aqueous solution, and a method of adding the raw zinc oxide to an alkaline aqueous solution and adjusting the pH at 10 or more. Further, a uniform slurry can be obtained by dispersing at 35° C. or less for 10 minutes or more after adjusting the pH.

The alkaline aqueous solution used for pH adjustment of the slurry of raw zinc oxide is not particularly limited but may include sodium hydroxide aqueous solution, potassium hydroxide aqueous solution, and ammonia water.

In the slurry of raw zinc oxide, components other than raw zinc oxide, water, and an alkaline aqueous solution may be added in a small amount within the bounds of not impairing the effect of the present disclosure. For example, a dispersant and the like may be added.

In the production method of the present disclosure, a step (step (2)) of mixing the slurry of raw zinc oxide prepared in the step (step (1)) with a zinc salt aqueous solution at 35° C. or less is carried out. It is preferred that the reactivity between the raw zinc oxide and the zinc salt aqueous solution may be controlled and a particle growth may be increased by mixing at 35° C. or less. The reaction temperature is more preferably 30° C. or less, still more preferably 20° C. or less.

The zinc salt aqueous solution is not particularly limited, and examples thereof may include aqueous solutions of zinc acetate, zinc nitrate, zinc sulfate, zinc chloride and zinc formate. Particularly when a zinc acetate aqueous solution, among the zinc salt aqueous solutions, is used, specific hexagonal plate-shaped zinc oxide particles of the present disclosure can be suitably obtained.

These zinc salt aqueous solutions may be those prepared by mixing zinc oxide, an acid and water to acid-hydrolyze the zinc oxide. The particle shape and particle diameter of the zinc oxide to be used when the zinc salt aqueous solution is prepared with zinc oxide, an acid and water are not particularly limited, but the Zn purity of zinc oxide is preferably 95% or more for reducing impurities as much as possible. Examples of the acid include acetic acid, nitric acid, sulfuric acid, hydrochloric acid, formic acid, citric acid, oxalic acid, propionic acid, malonic acid, lactic acid, tartaric acid, gluconic acid and succinic acid, and particularly when acetic acid is used, specific hexagonal plate-shaped zinc oxide particles of the present disclosure can be suitably obtained. Two of these zinc salt aqueous solutions may be used in combination.

The zinc salt concentration in the zinc salt aqueous solution is preferably more than 0.1 mol/l and 4.0 mol/l or less, and particularly the zinc salt concentration in the zinc salt aqueous solution is preferably more than 0.2 mol/l and 2.0 mol/l or less.

In the zinc salt aqueous solution, components other than the zinc salt and water may be added in a small amount within the bounds of not impairing the effect of the present disclosure. For example, a dispersant and the like may be added.

As a method for mixing the two liquids, a method of adding the water slurry of raw zinc oxide and the zinc salt aqueous solution at the same time to temperature controlled water; a method of adding the water slurry of raw zinc oxide to the zinc salt aqueous solution while maintaining the temperature; and a method of adding the zinc salt aqueous solution to the water slurry of raw zinc oxide while maintaining the temperature.

The production method of the present disclosure comprises a step (3) of aging the mixed slurry obtained by the above-mentioned steps (step (1) and step (2)) with heating.

Hexagonal plate-shaped zinc oxide particles having an intended shape and particle diameter can be obtained by the aging with heating.

Preferably, the aging is performed at 45 to 110° C. The aging time may be 0.5 to 24 hours. The particle diameter can be adjusted by conditions such as an aging temperature, an aging time, a raw zinc oxide concentration and a zinc salt concentration, and therefore it is preferable to appropriately set these conditions according to intended hexagonal plate-shaped zinc oxide particles.

Hexagonal plate-shaped zinc oxide particles thus obtained may be subjected to post-treatments such as filtration, water washing and drying as necessary.

Hexagonal plate-shaped zinc oxide particles produced by the above-described method may be classified by sieving as necessary. Examples of methods for classification by sieving may include wet classification and dry classification. Further, a treatment such as wet crushing or dry crushing may be performed.

As described above, the method for production of hexagonal plate-shaped zinc oxide particles according to the present disclosure is capable of obtaining hexagonal plate-shaped zinc oxide particles without performing a calcinating treatment, but hexagonal plate-shaped zinc oxide particles obtained by the above-described method may be subjected to a calcinating treatment. For calcinating, mention may be made of a known method using an arbitrary device, and treatment conditions and the like are not particularly limited.

The hexagonal plate-shaped zinc oxide particle of the present disclosure may be subjected to an additional surface treatment. The surface treatment is not particularly limited but includes a surface treatment to form a layer of at least one compound selected from the group consisting of silicon oxides, hydrates of silicon oxide, aluminum oxides, and aluminum hydroxides, a surface treatment using a water-repellent organic compound, and a surface treatment using a coupling agent such as silane coupling agents and titanium coupling agents. These surface treatments may be used in combination.

The formation of a layer using at least one compound selected from the group consisting of silicon oxides, hydrates of silicon oxide, aluminum oxides, and aluminum hydroxides may be done by a method of depositing a Si source compound and/or Al source compound on a powder surface through hydrolysis or thermolysis. The Si source compound and/or Al source compound include compounds which can easily convert to $SiO_2$, $Al(OH)_3$, or $Al_2O_3$ such as tetraalkoxysilane and hydrolysis condensate thereof, sodium silicate, potassium silicate, aluminum alkoxide and hydrolysis condensate thereof, and sodium aluminate.

The hydrolysis reaction is not particularly limited but a method using an acid such as sulfuric acid, hydrochloric acid, acetic acid, and nitric acid may be used. A neutralizing method in the treatment method using the water dispersion may be any one of a method of adding the Si source compound and/or Al source compound after adding the acid to the dispersion containing the hexagonal plate-shaped zinc oxide particles, a method of adding the acid after adding the Si source compound and/or Al source compound to the dispersion, and a method of adding the acid and the Si source compound and/or Al source compound at the same time to the dispersion.

The treatment with the water repellent organic compound is not particularly limited but includes a treatment using silicone oils, alkylsilanes, alkyltitanates, alkylaluminates, polyolefins, polyesters, metal soaps, amino acids, or amino acid salts. Among them, silicone oils are preferred because of good chemical stability. The specific example of the silicone oil includes dimethylpolysiloxane (for example, KF-96A-100cs manufactured by Shin-Etsu Chemical Co., Ltd., DM10 manufactured by wacker asahikasei silicone co., ltd.), methyl hydrogen polysiloxane (for example, KF-99P manufactured by Shin-Etsu Chemical Co., Ltd., SH1107C manufactured by Dow corning Toray), (dimethicone/methicone) copolymer (for example, KF-9901 manufactured by Shin-Etsu Chemical Co., Ltd.), methyl phenyl silicone (for example, KF-50-100cs manufactured by Shin-Etsu Chemical Co., Ltd.), amino modified silicone (for example, KF-8015 manufactured by Shin-Etsu Chemical Co., Ltd., JP-8500 Conditioning agent manufactured by Dow corning Toray, ADM6060 manufactured by wacker asahikasei silicone co., ltd.), triethoxysilylethyl polydimethylsiloxyethyl dimethicone (for example, KF-9908 manufactured by Shin-Etsu Chemical Co., Ltd.), and triethoxysilylethyl polydimethylsiloxyethyl hexyl dimethicone (for example, KF-9909 manufactured by Shin-Etsu Chemical Co., Ltd.).

The silane coupling agent includes vinyltris(2-methoxyethoxy)silane, vinyl trichlorosilane, vinyltrimethoxysilane, vinyltriethoxysilane, 2-(3,4 epoxy cyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropyl methyldimethoxysilane, 3-methacryloxypropyl trimethoxysilane, 3-methacryloxypropyl methyldiethoxysilane, 3-methacryloxypropyl triethoxysilane, 3-acryloxypropyl trimethoxysilane, N-2(aminoethyl) 3-aminopropylmethyldimethoxysilane, N-2(aminoethyl) 3-aminopropyltrimethoxysilane, N-2(aminoethyl) 3-aminopropyltriethoxysilane, 3-aminopropyltrimethoxysilane, 3-aminotriethoxysilane, 3-triethoxysilyl-N-(1,3 dimethylbutylidene) propylamine, N-phenyl-3-aminopropyltrimethoxysilane, N-(vinylbenzyl)-2-aminoethyl-3-aminopropyltrimethoxysilane hydrochloride, 3-ureidopropyltriethoxysilane, 3-chloropropyltrimethoxysilane, 3-mercaptopropylmethyldimethoxysilane, 3-mercaptopropyltrimethoxysilane, bis(triethoxysilylpropyl)tetrasulfide, 3-isocyanatepropyltriethoxysilane, tetramethoxysilane, tetraethoxysilane, methyltrimethoxysilane, methyltriethoxysilane, methyltriethoxysilane, phenyltriethoxysilane, hexamethyldisilazane, hexyltrimethoxysilane, and decyltrimethoxysilane.

The titanium coupling agent includes tetraisopropyl titanate, tetra-n-butyltitanate, butyltitanate dimer, tetra(2-ethylhexyl)titanate, tetramethyl titanate, titanium acetylacetonate, titanium tetraacetylacetonate, titanium ethylacetoacetate, titanium octanedioleate, titanium lactate, titanium triethanolaminato, and polyhydroxy titanium stearate.

The surface treatment is preferably done so that the surface treating amount is 1 to 10 wt % relative to the treated powder as whole. It is preferred to adjust the treating amount within the above-mentioned range because the smoothness and the humidity resistance can be improved to raise the dispersibility in a resin.

The hexagonal plate-shaped zinc oxide particle of the present disclosure may be used for a cosmetic, an ink, a coating, and a plastic in combination or mixed with other components. The zinc oxide particle especially has the above-mentioned properties so that the cosmetic containing the same which shows a proper powder touch with good slippage and less roughness can be preferably obtained.

The cosmetic is not particularly limited. Cosmetics for ultraviolet prevention such as a sunscreen agent; cosmetics for base make up such as a foundation; and cosmetics for point make up such as a lipstick can be obtained by mixing the composite powder with any cosmetic raw material, as necessary. When used in cosmetics, excellent performances can be achieved because the hexagonal plate-shaped zinc oxide particles of the present disclosure have the ultraviolet shielding ability in addition to the above-mentioned excellent powder touch.

The cosmetic can be in any form, for example, a form of an oil-based cosmetic, a water-based cosmetic, an O/W type cosmetic, or a W/O type cosmetic.

The cosmetic may contain any water-based component or an oil-based component which can be used in the cosmetic field. The water-based component and the oil-based component may contain any component, including, but not limited to, for example, an oil solution, a surfactant, a humectant, a higher alcohol, a sequestering agent, a natural or synthetic polymer, a water-soluble or oil-soluble polymer, an ultraviolet shielding agent, various extracts, a coloring agent such as an organic dye, a preservative, an antioxidant, a colorant, a thickener, a pH adjuster, a perfume, a cooling-sensation agent, an antiperspirant, a bactericidal agent, a skin activating agent, and various powders.

Examples of the oil solution include, but not limited to, for example, natural animal and plant fats (for example, olive oil, mink oil, castor oil, palm oil, beef tallow, evening primrose oil, coconut oil, castor oil, cacao oil, and macadamia nut oil); waxes (for example, jojoba oil, beeswax, lanolin, carnauba wax, and candelilla wax); higher alcohols (for example, lauryl alcohol, stearyl alcohol, cetyl alcohol, and oleyl alcohol); higher fatty acids (for example, lauric acid, palmitic acid, stearic acid, oleic acid, behenic acid, and lanolin fatty acid); higher aliphatic hydrocarbons (for example, liquid paraffin, solid paraffin, squalane, vaseline, ceresin, and microcrystalline wax); synthetic ester oils (for example, butyl stearate, hexyl laurate, diisopropyl adipate, diisopropyl sebacate, octyldodecyl myristate, isopropyl myristate, isopropyl palmitate, isopropyl myristate, cetyl isooctanoate, and neopentyl glycol dicaprate); and silicone derivatives (for example, silicone oils such as methyl silicone and methyl phenyl silicone). Further, an oil-soluble vitamin, a preservative, or a whitening agent may be blended.

Examples of the surfactant include a lipophilic nonionic surfactant and a hydrophilic nonionic surfactant. Examples of the lipophilic nonionic surfactant include, but not limited to, for example, sorbitan monooleate, sorbitan monoisostearate, sorbitan monolaurate, sorbitan monopalmitate, sorbitan monostearate, sorbitan sesquioleate, sorbitan trioleate, sorbitan fatty acid esters such as diglycerol sorbitan penta-2-ethylhexylate and diglycerol sorbitan tetra-2-ethylhexylate, glycerin fatty acids such as glycerol mono-cottonseed oil fatty acid, glycerol monoerucate, glycerol sesquioleate, glycerol monostearate, α,α'-glycerol oleate pyroglutamate, and glycerol monostearate malate; propylene glycol fatty acid esters such as propylene glycol monostearate; hydrogenated castor oil derivatives; and glycerol alkyl ethers.

Examples of the hydrophilic nonionic surfactant include, but not limited to, for example, POE sorbitan fatty acid esters such as POE sorbitan monooleate, POE sorbitan monostearate, and POE sorbitan tetraoleate; POE sorbit fatty acid esters such as POE sorbit monolaurate, POE sorbit monooleate, POE sorbit pentaoleate, and POE sorbit monostearate; POE glycerin fatty acid esters such as POE glycerin monostearate, POE glycerin monoisostearate, and POE glycerin triisostearate; POE fatty acid esters such as POE monooleate, POE distearate, POE monodioleate, and distearic acid ethylene glycol; POE alkyl ethers such as POE lauryl ether, POE oleyl ether, POE stearyl ether, POE behenyl ether, POE 2-octyl dodecyl ether, and POE cholestanol ether; POE alkyl phenyl ethers such as POE octyl phenyl ether, POE nonyl phenyl ether, and POE dinonyl phenyl ether; Pluaronic types such as Pluronic; POE/POP alkyl ethers such as POE/POP cetyl ether, POE/POP2-decyl tetradecyl ether, POE/POP monobutyl ether, POE/POP hydrogenated lanolin, and POE/POP glycerin ether; tetra POE/tetra POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester, and POE hydrogenated castor oil maleic acid; POE beeswax/lanolin derivatives such as POE sorbit beeswax; alkanolamides such as coconut oil fatty acid diethanolamide, lauric acid monoethanolamide, and fatty acid isopropanolamide; POE propylene glycol fatty acid esters, POE alkylamines, POE fatty acid amides, sucrose fatty acid esters, POE nonyl phenyl formaldehyde condensation products, alkyl ethoxydimethylamine oxides, and trioleyl phosphates.

Any other surfactant may be blended, including, for example, anionic surfactants such as fatty acid soaps, higher alkyl sulfate ester salts, POE lauryl sulfate triethanolamine, and alkyl ether sulfate ester salts; cationic surfactants such as alkyl trimethyl ammonium salts, alkyl pyridinium salts, alkyl quaternized ammonium salts, alkyl dimethyl benzylammonium salts, POE alkylamines, alkylamine salts, and polyamine fatty acid derivatives; and amphoteric surfactants such as an imidazoline-based amphoteric surfactant and a betaine-based surfactant, as long as the surfactant does not affect the stability and skin irritation.

Examples of the humectant include, but not limited to, for example, xylitol, sorbitol, maltitol, chondroitin sulfate, hyaluronic acid, mucoitinsulfuric acid, caronic acid, atelocollagen, cholesteryl-12-hydroxystearate, sodium lactate, bile salt, dl-pyrrolidone carboxylate salts, short chain soluble collagen, (EO)PO adducts of diglycerin, *Rosa Roxburghii* Fruit extract, yarrow extract, and melilot extract.

Examples of the higher alcohol include, but not limited to, for example, linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerin ether (batyl alcohol), 2-decyl tetradecinol, lanolin alcohol, cholesterol, phytosterol, hexyldodecanol, isostearyl alcohol, and octyl dodecanol.

Examples of the sequestering agent include, but not limited to, for example, 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

Examples of the natural water-soluble polymer include, but not limited to, for example, plant polymers such as gum arabic, tragacanth gum, galactan, guar gum, carob gum, karaya gum, carrageenan, pectin, agar, quince seed (*Cydonia oblonga*), algae colloid (brown alga extract), starch (rice, corn, potato, wheat), and glycyrrhizinic acid; microbial polymers such as xanthan gum, dextran, succinoglycan, and pullulan; and animal polymers such as collagen, casein, albumin, and gelatin.

Examples of the semisynthetic water-soluble polymer include, but not limited to, for example, starch polymers such as carboxymethyl starch and methyl hydroxypropyl starch; cellulose polymers such as methylcellulose, nitrocellulose, ethylcellulose, methyl hydroxypropyl cellulose, hydroxyethyl cellulose, cellulose sodium sulfate, hydroxypropyl cellulose, sodium carboxymethyl cellulose (CMC), crystalline cellulose, and cellulose powder; and alginate polymers such as sodium alginate and alginic acid propylene glycol ester.

Examples of the synthetic water-soluble polymer include, but not limited to, for example, vinyl polymers such as polyvinyl alcohol, polyvinyl methyl ether, and polyvinylpyrrolidone; polyoxyethylene polymers such as polyethylene glycol 20,000, 40,000, and 60,000; copolymers such as a polyoxyethylene polyoxypropylene copolymer; acrylic polymers such as sodium polyacrylate, polyethyl acrylate, and polyacrylamide; polyglycerin, polyethylenimine, cationic polymer, carboxyvinyl polymer, alkyl-modified carboxyvinyl polymer, (hydroxyethyl acrylate/acryloyl dimethyl taurine Na)copolymer, (acrylate Na/acryloyl dimethyl taurine Na)copolymer, (acryloyl dimethyl taurine ammonium/vinylpyrrolidone) copolymer, (acryloyl dimethyl taurine ammonium methacrylate beheneth-25) crosspolymer.

Examples of the inorganic water-soluble polymer include, but not limited to, for example, bentonite, magnesium aluminum silicate (Veegum), laponite, hectorite, and silicic anhydride.

Examples of the ultraviolet shielding agent include, but not limited to, for example, benzoic acid-based ultraviolet shielding agents such as p-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthranilic acid-based ultraviolet shielding agents such as homomenthyl-N-acetyl anthranilate; salicylic acid-based ultraviolet shielding agents such as amyl salicylate, menthyl salicylate, homomenthyl salicylate, octyl salicylate, phenyl salicylate, benzyl salicylate, and p-isopropanol phenyl salicylate; cinnamic acid-based ultraviolet shielding agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl-diparamethoxy cinnamate; benzophenone-based ultraviolet shielding agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methyl benzophenone, 2-hydroxy-4-methoxybenzophenone-5-sulfonate, 4-phenyl benzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methyl benzoxazole, 2,2'-hydroxy-5-methyl phenyl benzotriazole, 2-(2'-hydroxy-5'-t-octylphenyl)benzotriazole, 2-(2'-hydroxy-5'-methylphenyl benzotriazole, dibenzalazine, dianisoylmethane, 4-methoxy-4'-t-butyldibenzoylmethane, and 5-(3,3-dimethyl-2-norbornylidene)-3-pentan-2-one.

Examples of the other chemical component include, but not limited to, for example, vitamins such as vitamin A oil, retinol, retinol palmitate, inosit, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), dl-α-tocopherol, DL-α-tocopherol acetate, pantothenic acid, and biotin; hormones such as estradiol and ethinyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor; sulfur, lysozyme chloride, and pyridoxine chloride.

Examples of various extracts include, but not limited to, for example, *Houttuynia cordata* extract, Phellodendron bark extract, melilot extract, dead nettle extract, licorice extract, peony root extract, soapwort extract, luffa extract, cinchona extract, strawberry geranium extract, sophora root extract, nuphar extract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, hamamelis extract, placenta extract, thymic extract, silk extract, and licorice extract.

Examples of various powders include luster color pigments such as red iron oxide, yellow iron oxide, black iron oxide, mica titanium, iron oxide-coated mica titanium, and titanium oxide-coated glass flake; inorganic powders such as mica, talc, kaolin, sericite, titanium dioxide, and silica; and organic powders such as polyethylene powder, nylon powder, crosslinked polystyrene, cellulose powder, and silicone powder. Preferably, some or all of powder components are hydrophobized with a material such as a silicone, a fluorine compound, a metallic soap, an oil solution, or an acyl glutamic acid salt by a known method in order to improve sensory characteristics and makeup retainability. Further, a composite powder other than the composite powder of the present disclosure may be blended and used.

When the hexagonal plate-shaped zinc oxide particle of the present disclosure is used as a component added to inks, colored pigments such as titanium oxide, red iron oxide, antimony red, cadmium yellow, cobalt blue, prussian blue, ultramarine, carbon black, and graphite; and extender pigments such as calcium carbonate, kaolin, clay, barium sulfate, aluminum hydroxide, and talc may be used in combination. Further, the above zinc oxide powder can be used with the organic pigment including pigment components such as a soluble azo pigment, an insoluble azo pigment, an azo lake pigment, a condensed azo pigment, a copper phthalocyanine pigment, and a condensed polycyclic pigment; binder resins such as a shellac resin, an acrylic resin, a styrene-acrylic resin, a styrene-maleic acid resin, a styrene-acrylic-maleic acid resin, a polyurethane resin, a polyester resin, and a polyamide resin; and water-miscible organic solvents.

When the hexagonal plate-shaped zinc oxide particle of the present disclosure is used as a component added to coating compositions, it can be used with film-forming resins such as an acrylic resin, a polyester resin, and an epoxy resin; various pigments such as a colored pigment, a extender pigment, and a luster pigment; a curing catalyst, a surface control agent, an antifoaming agent, a pigment dispersant, a plasticizer, a film-forming aid, an ultraviolet absorption agent, an antioxidant, and the like. A resin in the coating may be a curable or uncurable resin.

The present disclosure relates to a resin composition containing the above-mentioned hexagonal plate-shaped zinc oxide particles. This resin composition shows an excellent heat releasing property because the hexagonal plate-shaped zinc oxide particles act as a heat releasing filler. Further, the composition may be used as a resin composition having a superior infrared radiation reflective performance.

The hexagonal plate-shaped zinc oxide particles of the present disclosure have the infrared radiation reflective performance as mentioned above so that the particles may be used as an infrared radiation shielding material for various fields.

EXAMPLES

Hereinafter, the present disclosure will be explained with reference to examples. However, the present disclosure is not limited to these examples.

Example 1

To a slurry obtained by repulping raw zinc oxide (manufactured by Sakai Chemical Industry Co., Ltd., FINEX-50, particle diameter 0.02 μm) 40 g in 430.49 ml of water, 8 ml of 30% sodium hydroxide aqueous solution was added to adjust the pH at 13. The total amount of the above-mentioned slurry and 563.24 ml of zinc acetate aqueous solution with a zinc acetate concentration of 1.61 mol/l was added with stirring to 200 ml of water at a controlled temperature of 15° C. for 120 minutes so that a mixed slurry of zinc acetate aqueous solution and raw zinc oxide with a zinc acetate concentration of 0.75 mol/l was prepared. Next, the mixed slurry was heated to 95° C. over 160 minutes with stirring and aged at 95° C. for 1 hour with stirring. After aging, the slurry was quenched immediately, then filtered, washed, and dried at 110° C. for 12 hours to obtain hexagonal plate-shaped zinc oxide particles having a primary particle diameter of 3.13 μm. The size and form of the obtained particles were observed with a scanning electron microscope JSM-6510A (manufactured by JEOL Ltd.). The obtained electron microscope photograph is shown in FIG. 1. The obtained particles were analyzed by using an X-ray diffractometer UltimaIII (manufactured by Rigaku Corporation), and the obtained X-ray diffraction spectra was shown in FIG. 2. The results of evaluating the physical properties of the obtained particles are shown in Table 1.

Example 2

Figure 3:
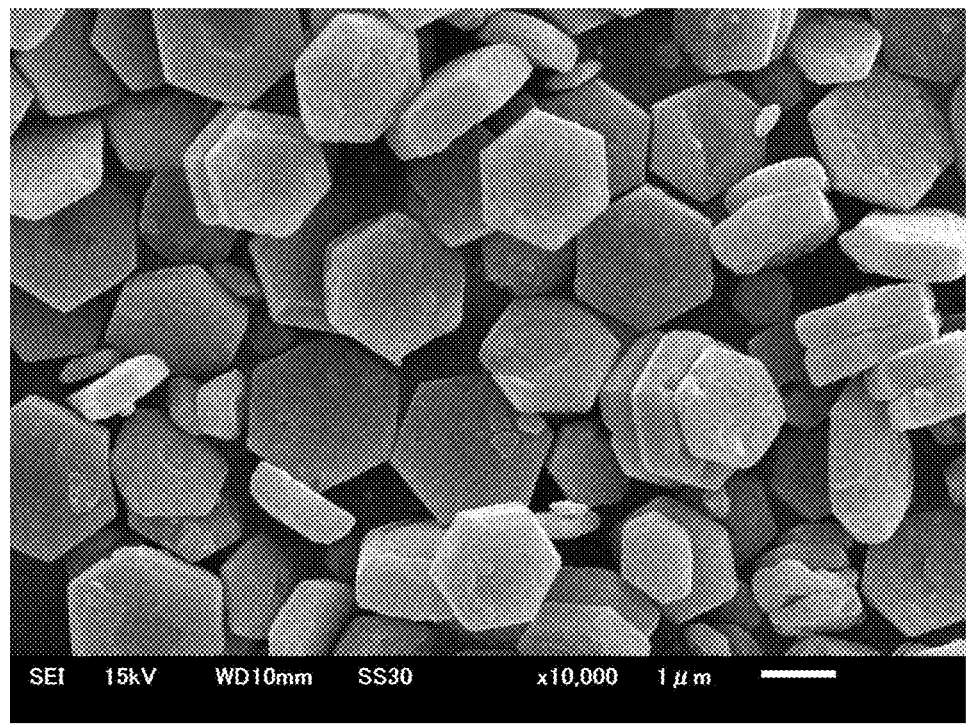
FIG. 3 is a scanning electron microscope photograph of zinc oxide particles of the present disclosure obtained in Example 2.

To a slurry obtained by repulping raw zinc oxide (manufactured by Sakai Chemical Industry Co., Ltd., FINEX-50, particle diameter 0.02 μm) 40 g in 430.49 ml of water, 8 ml of 30% sodium hydroxide aqueous solution was added to adjust the pH at 13. The total amount of the above-mentioned slurry and 563.24 ml of zinc acetate aqueous solution with a zinc acetate concentration of 1.61 mol/l was added with stirring to 200 ml of water at a controlled temperature of 30° C. for 120 minutes so that a mixed slurry of zinc acetate aqueous solution and raw zinc oxide with a zinc acetate concentration of 0.75 mol/l was prepared. Next, the mixed slurry was heated to 95° C. over 130 minutes with stirring and aged at 95° C. for 1 hour with stirring. After aging, the slurry was quenched immediately, then filtered, washed, and dried at 110° C. for 12 hours to obtain hexagonal plate-shaped zinc oxide particles having a primary particle diameter of 1.89 μm. The size and form of the obtained particles were observed with a scanning electron microscope JSM-6510A (manufactured by JEOL Ltd.). The obtained electron microscope photograph is shown in FIG. 3. The results of evaluating the physical properties of the obtained particles are shown in Table 1.

Example 3

Figure 4:
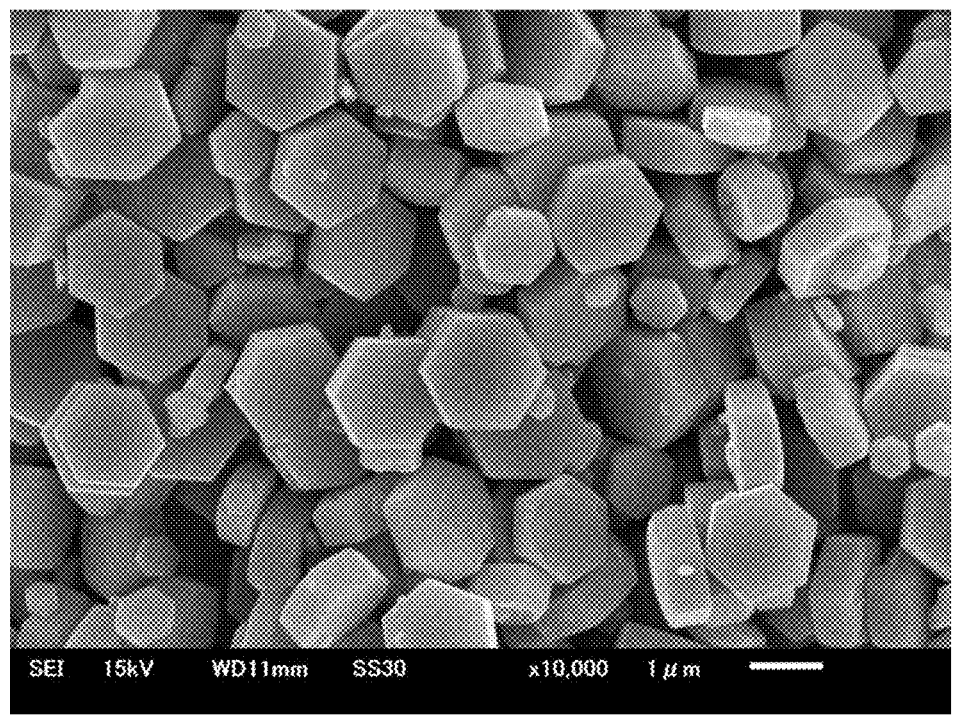
FIG. 4 is a scanning electron microscope photograph of zinc oxide particles of the present disclosure obtained in Example 3.

To a slurry obtained by repulping raw zinc oxide (manufactured by Sakai Chemical Industry Co., Ltd., FINEX-50, particle diameter 0.02 μm) 40 g in 430.49 ml of water, 70 ml of 30% sodium hydroxide aqueous solution was added to adjust the pH at 14. The total amount of the above-mentioned slurry and 563.24 ml of zinc acetate aqueous solution with a zinc acetate concentration of 1.61 mol/l was added with stirring to 200 ml of water at a controlled temperature of 30° C. for 120 minutes so that a mixed slurry of zinc acetate aqueous solution and raw zinc oxide with a zinc acetate concentration of 0.75 mol/l was prepared. Next, the mixed slurry was heated to 95° C. over 130 minutes with stirring and aged at 95° C. for 1 hour with stirring. After aging, the slurry was quenched immediately, then filtered, washed, and dried at 110° C. for 12 hours to obtain hexagonal plate-shaped zinc oxide particles having a primary particle diameter of 1.48 μm. The size and form of the obtained particles were observed with a scanning electron microscope JSM-6510A (manufactured by JEOL Ltd.). The obtained electron microscope photograph is shown in FIG. 4. The results of evaluating the physical properties of the obtained particles are shown in Table 1.

Example 4

Figure 5:
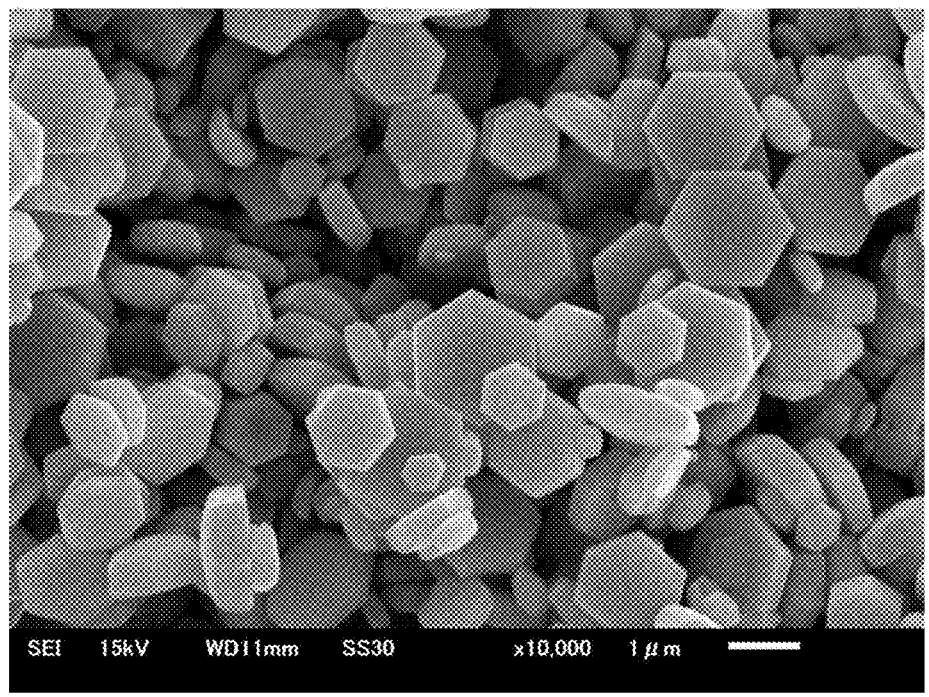
FIG. 5 is a scanning electron microscope photograph of zinc oxide particles of the present disclosure obtained in Example 4.

To a slurry obtained by repulping raw zinc oxide (manufactured by Sakai Chemical Industry Co., Ltd., FINEX-50, particle diameter 0.02 μm) 40 g in 430.49 ml of water, 0.1 ml of 30% sodium hydroxide aqueous solution was added to adjust the pH at 10. The total amount of the above-mentioned slurry and 563.24 ml of zinc acetate aqueous solution with a zinc acetate concentration of 1.61 mol/l was added with stirring to 200 ml of water at a controlled temperature of 15° C. for 120 minutes so that a mixed slurry of zinc acetate aqueous solution and raw zinc oxide with a zinc acetate concentration of 0.75 mol/l was prepared. Next, the mixed slurry was heated to 95° C. over 160 minutes with stirring and aged at 95° C. for 1 hour with stirring. After aging, the slurry was quenched immediately, then filtered, washed, and dried at 110° C. for 12 hours to obtain hexagonal plate-shaped zinc oxide particles having a primary particle diameter of 1.32 µm. The size and form of the obtained particles were observed with a scanning electron microscope JSM-6510A (manufactured by JEOL Ltd.). The obtained electron microscope photograph is shown in FIG. 5. The results of evaluating the physical properties of the obtained particles are shown in Table 1.

Example 5

Figure 6:
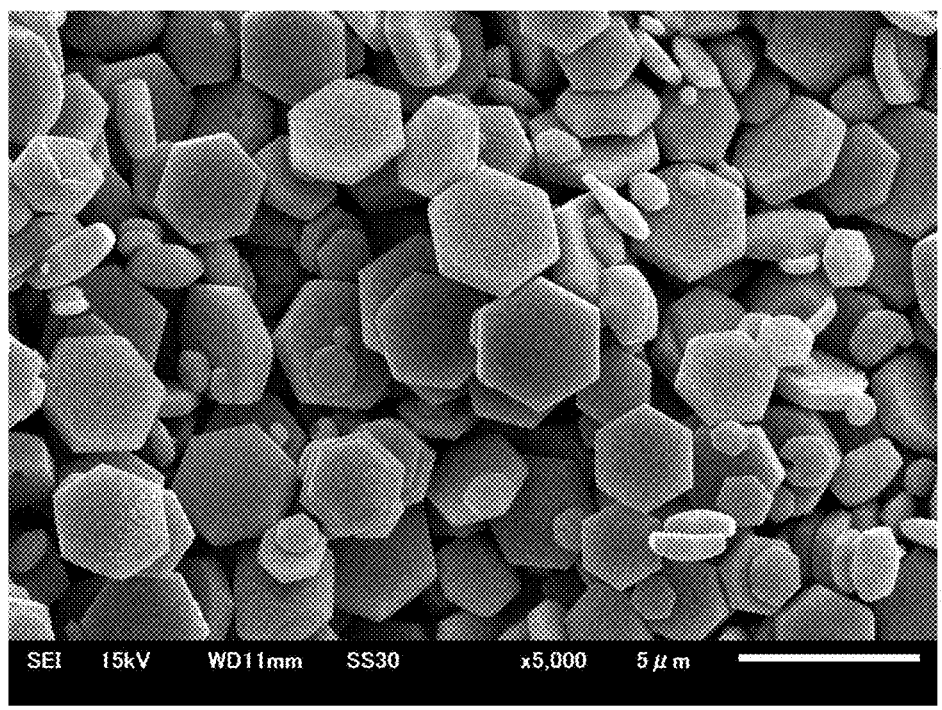
FIG. 6 is a scanning electron microscope photograph of zinc oxide particles of the present disclosure obtained in Example 5.

To a slurry obtained by repulping raw zinc oxide (manufactured by Sakai Chemical Industry Co., Ltd., FINEX-50, particle diameter 0.02 µm) 40 g in 430.49 ml of water, 8 ml of 30% sodium hydroxide aqueous solution was added to adjust the pH at 13. The total amount of the above-mentioned slurry and 563.24 ml of zinc acetate aqueous solution with a zinc acetate concentration of 1.61 mol/l was added with stirring to 200 ml of water at a controlled temperature of 15° C. for 120 minutes so that a mixed slurry of zinc acetate aqueous solution and raw zinc oxide with a zinc acetate concentration of 0.75 mol/l was prepared. Next, the mixed slurry was heated to 95° C. over 160 minutes with stirring and aged at 95° C. for 5 hours with stirring. After aging, the slurry was quenched immediately, then filtered, washed, and dried at 110° C. for 12 hours to obtain hexagonal plate-shaped zinc oxide particles having a primary particle diameter of 2.94 µm. The size and form of the obtained particles were observed with a scanning electron microscope JSM-6510A (manufactured by JEOL Ltd.). The obtained electron microscope photograph is shown in FIG. 6. The results of evaluating the physical properties of the obtained particles are shown in Table 1.

Comparative Example 1

Figure 7:
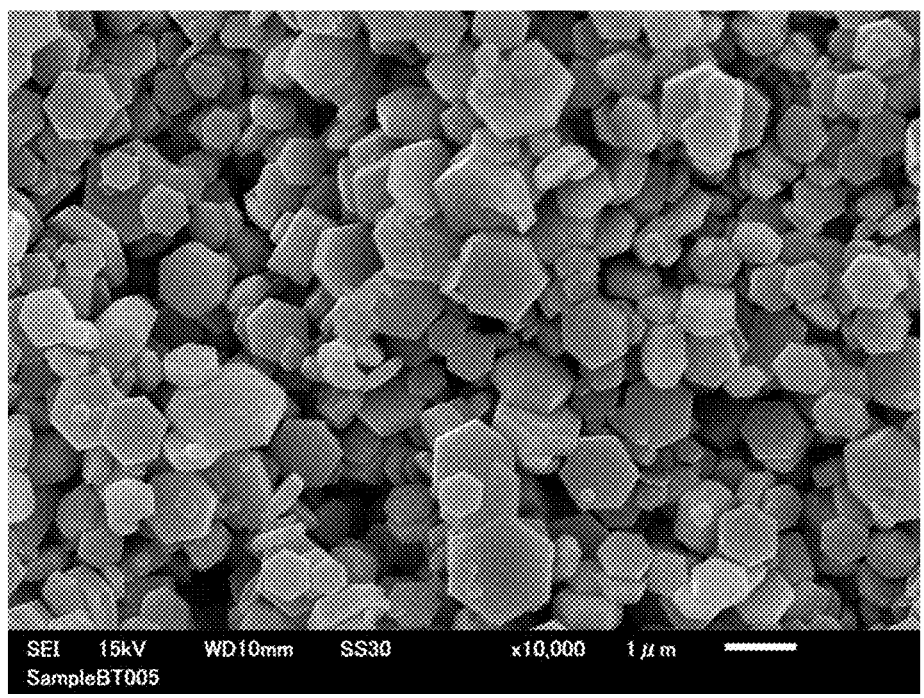
FIG. 7 is a scanning electron microscope photograph of zinc oxide particles of the present disclosure obtained in Comparative Example 1.

Raw zinc oxide (manufactured by Sakai Chemical Industry Co., Ltd., FINEX-50, particle diameter 0.02 µm) 80 g was added to 1200 ml of zinc acetate aqueous solution with a zinc acetate concentration of 1 mol/l to obtain a slurry and mixed at 25° C. for 0.5 hour. Next, the slurry was heated to 100° C. over 60 minutes with stirring and aged at 100° C. for 7 hours with stirring. After aging, the slurry was quenched immediately, then filtered, washed, and dried at 110° C. for 12 hours to obtain hexagonal plate-shaped zinc oxide particles having a primary particle diameter of 1.00 µm. The size and form of the obtained particles were observed with a scanning electron microscope JSM-6510A (manufactured by JEOL Ltd.). The obtained electron microscope photograph is shown in FIG. 7. The results of evaluating the physical properties of the obtained particles are shown in Table 2.

Comparative Example 2

Figure 8:
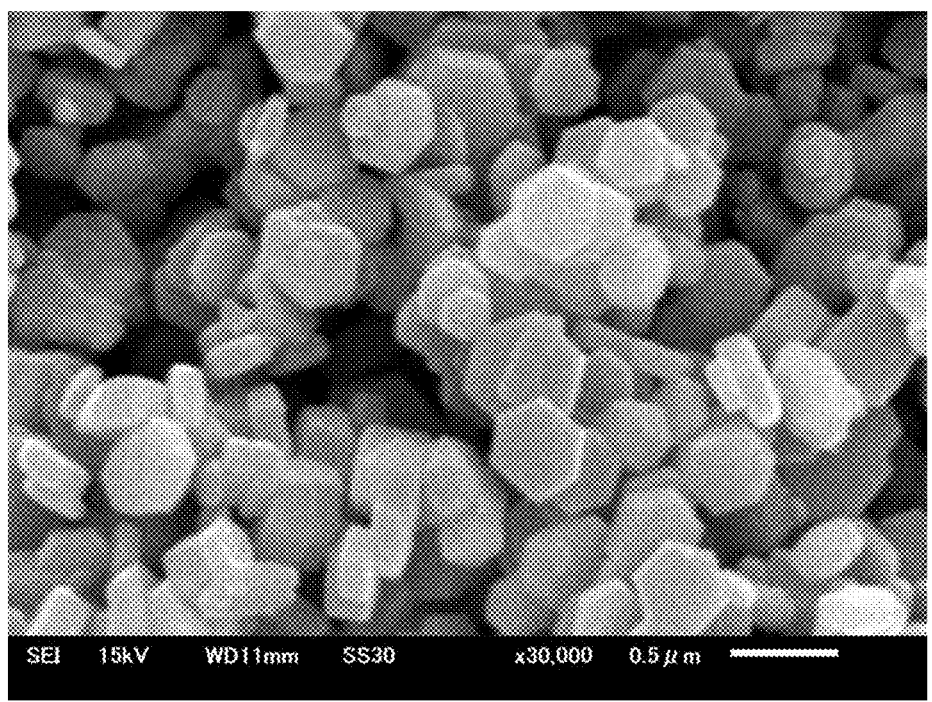
FIG. 8 is a scanning electron microscope photograph of zinc oxide particles of the present disclosure obtained in Comparative Example 2.

Raw zinc oxide (manufactured by Sakai Chemical Industry Co., Ltd., FINEX-50, particle diameter 0.02 µm) 80 g was added to 1200 ml of zinc acetate aqueous solution with a zinc acetate concentration of 1 mol/l to obtain a slurry and mixed at 25° C. for 0.5 hour. Next, the slurry was heated to 100° C. over 60 minutes with stirring and aged at 100° C. for 1 hour with stirring. After aging, the slurry was quenched immediately, then filtered, washed, and dried at 110° C. for 12 hours to obtain hexagonal plate-shaped zinc oxide particles having a primary particle diameter of 0.31 µm. The size and form of the obtained particles were observed with a scanning electron microscope JSM-6510A (manufactured by JEOL Ltd.). The obtained electron microscope photograph is shown in FIG. 8. The results of evaluating the physical properties of the obtained particles are shown in Table 2.

Comparative Example 3

Figure 9:
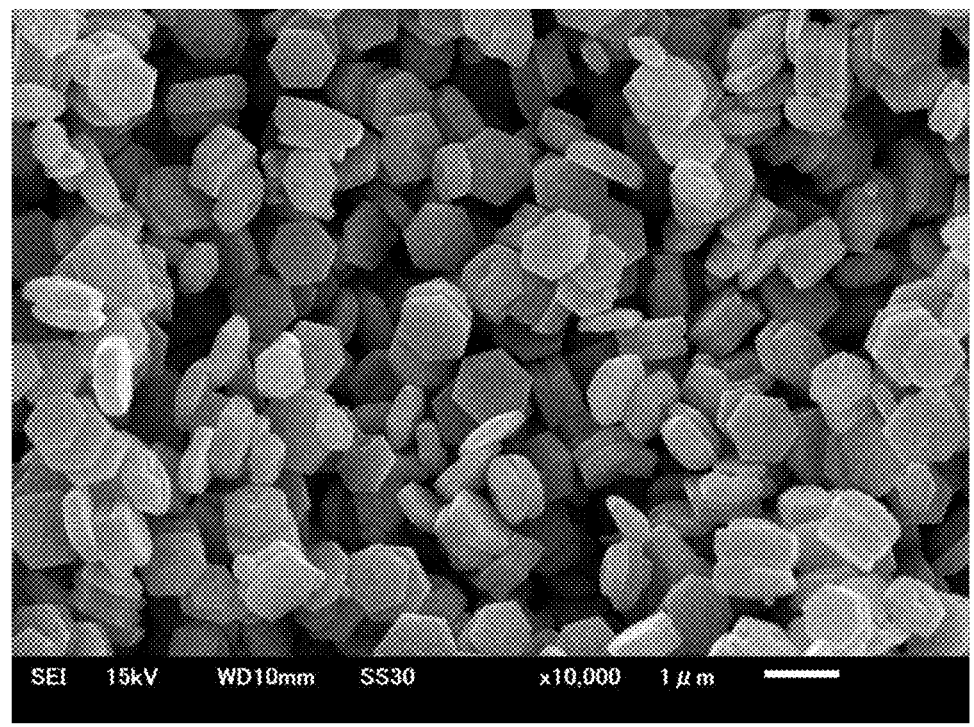
FIG. 9 is a scanning electron microscope photograph of zinc oxide particles of the present disclosure obtained in Comparative Example 3.

To a slurry obtained by repulping raw zinc oxide (manufactured by Sakai Chemical Industry Co., Ltd., FINEX-50, particle diameter 0.02 µm) 40 g in 430.49 ml of water, 8 ml of 30% sodium hydroxide aqueous solution was added to adjust the pH at 13. The total amount of the above-mentioned slurry and 563.24 ml of zinc acetate aqueous solution with a zinc acetate concentration of 1.61 mol/l was added with stirring to 200 ml of water at a controlled temperature of 40° C. for 120 minutes so that a mixed slurry of zinc acetate aqueous solution and raw zinc oxide with a zinc acetate concentration of 0.75 mol/l was prepared. Next, the mixed slurry was heated to 95° C. over 110 minutes with stirring and aged at 95° C. for 1 hour with stirring. After aging, the slurry was quenched immediately, then filtered, washed, and dried at 110° C. for 12 hours to obtain hexagonal plate-shaped zinc oxide particles having a primary particle diameter of 0.97 µm. The size and form of the obtained particles were observed with a scanning electron microscope JSM-6510A (manufactured by JEOL Ltd.). The obtained electron microscope photograph is shown in FIG. 9. The results of evaluating the physical properties of the obtained particles are shown in Table 2.

Comparative Example 4

Figure 10:
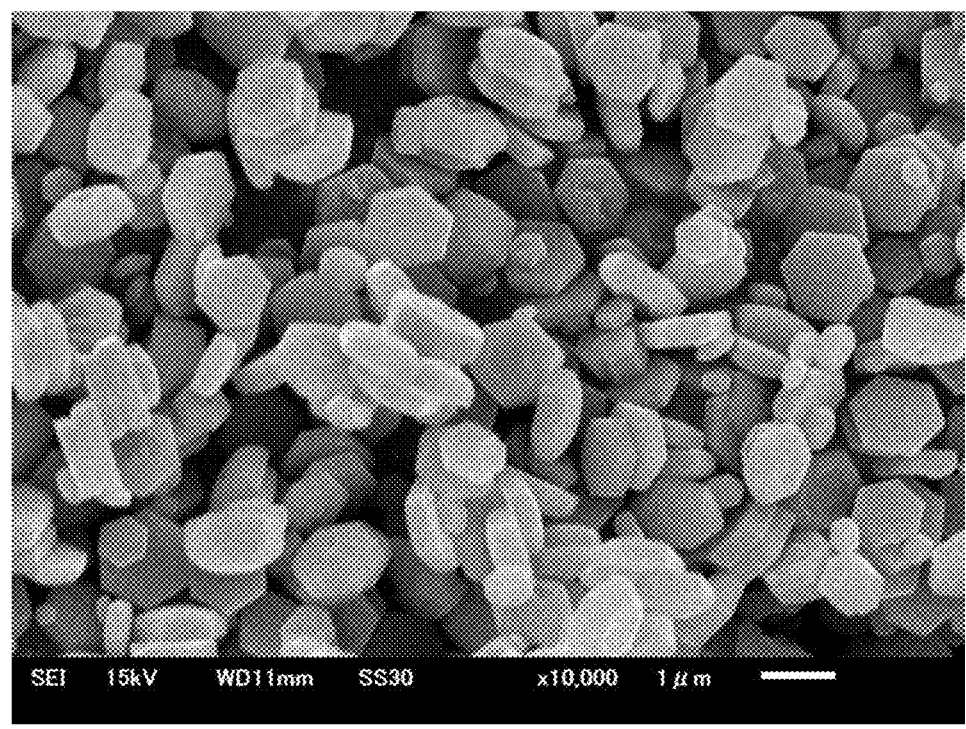
FIG. 10 is a scanning electron microscope photograph of zinc oxide particles of the present disclosure obtained in Comparative Example 4.

Raw zinc oxide (manufactured by Sakai Chemical Industry Co., Ltd., FINEX-50, particle diameter 0.02 µm) 40 g was repulped in 430.49 ml of water to obtain a slurry having a pH of 8. The total amount of the above-mentioned slurry and 563.24 ml of zinc acetate aqueous solution with a zinc acetate concentration of 1.61 mol/l was added with stirring to 200 ml of water at a controlled temperature of 30° C. for 120 minutes so that a mixed slurry of zinc acetate aqueous solution and raw zinc oxide with a zinc acetate concentration of 0.75 mol/l was prepared. Next, the mixed slurry was heated to 95° C. over 130 minutes with stirring and aged at 95° C. for 1 hour with stirring. After aging, the slurry was quenched immediately, then filtered, washed, and dried at 110° C. for 12 hours to obtain hexagonal plate-shaped zinc oxide particles having a primary particle diameter of 1.12 µm. The size and form of the obtained particles were observed with a scanning electron microscope JSM-6510A (manufactured by JEOL Ltd.). The obtained electron microscope photograph is shown in FIG. 10. The results of evaluating the physical properties of the obtained particles are shown in Table 2.

Comparative Example 5

Figure 11:
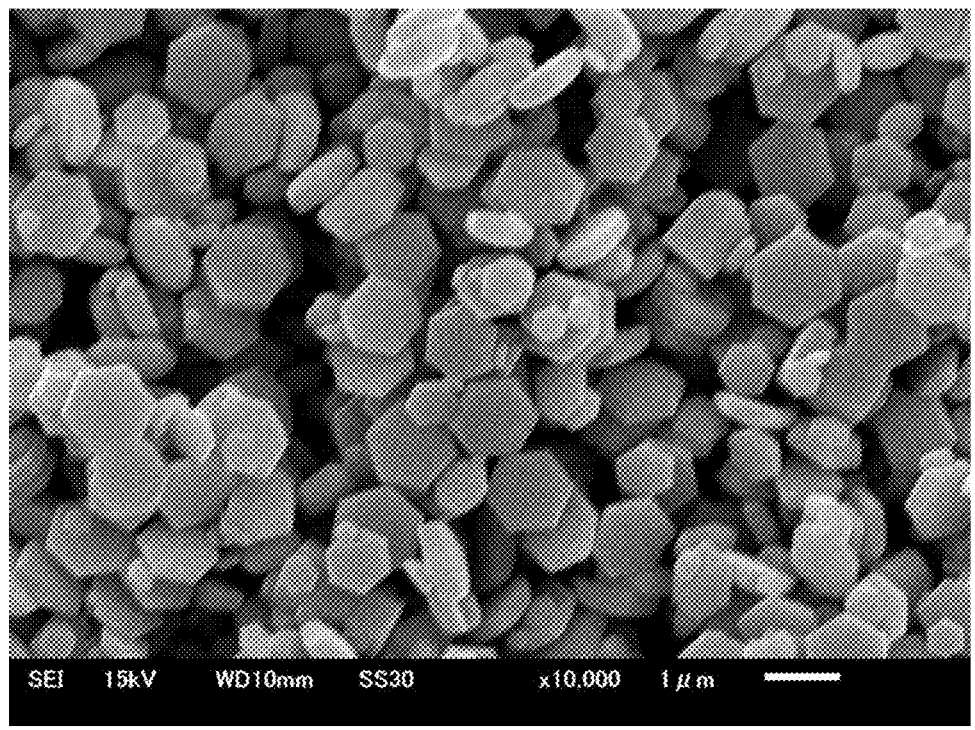
FIG. 11 is a scanning electron microscope photograph of zinc oxide particles of the present disclosure obtained in Comparative Example 5.

To a slurry obtained by repulping raw zinc oxide (manufactured by Sakai Chemical Industry Co., Ltd., FINEX-50, particle diameter 0.02 µm) 40 g in 430.49 ml of water, 10 ml of 90% acetic acid aqueous solution was added to adjust the pH at 6. The total amount of the above-mentioned slurry and 563.24 ml of zinc acetate aqueous solution with a zinc acetate concentration of 1.61 mol/l was added with stirring to 200 ml of water at a controlled temperature of 30° C. for 120 minutes so that a mixed slurry of zinc acetate aqueous solution and raw zinc oxide with a zinc acetate concentration of 0.75 mol/l was prepared. Next, the mixed slurry was heated to 95° C. over 130 minutes with stirring and aged at 95° C. for 1 hour with stirring. After aging, the slurry was quenched immediately, then filtered, washed, and dried at 110° C. for 12 hours to obtain hexagonal plate-shaped zinc oxide particles having a primary particle diameter of 0.96 μm. The size and form of the obtained particles were observed with a scanning electron microscope JSM-6510A (manufactured by JEOL Ltd.). The obtained electron microscope photograph is shown in FIG. 11. The results of evaluating the physical properties of the obtained particles are shown in Table 2.

Comparative Example 6

Figure 12:
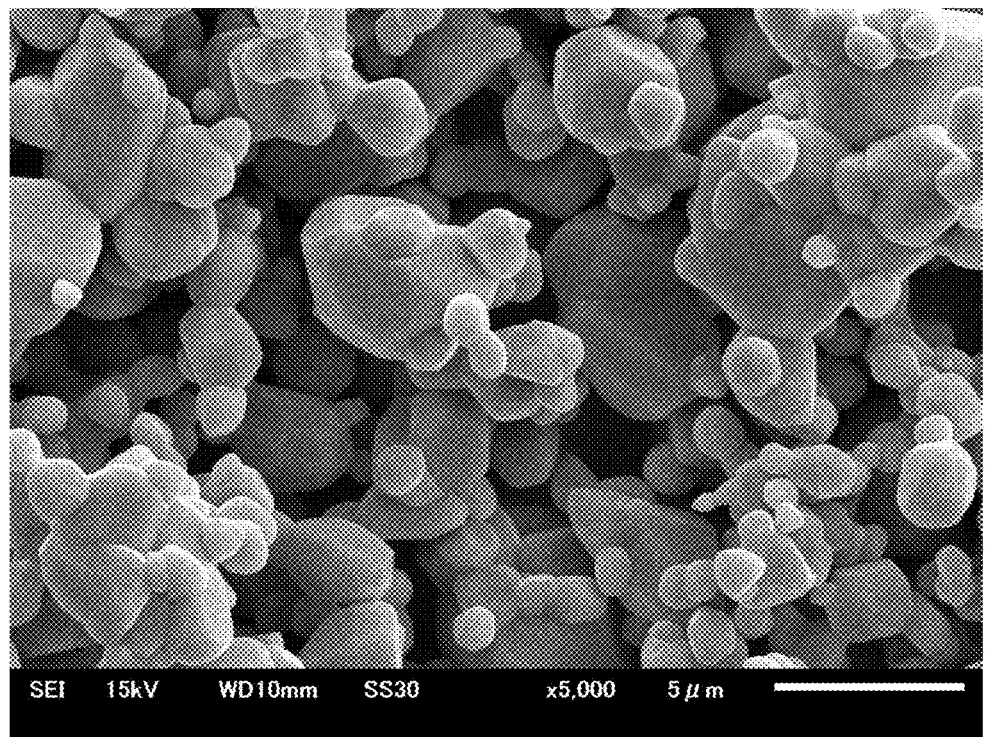
FIG. 12 is a scanning electron microscope photograph of zinc oxide particles of the present disclosure obtained in Comparative Example 6.

Raw zinc oxide (manufactured by Sakai Chemical Industry Co., Ltd., ZINC OXIDE NO. 1, particle diameter 0.6 μm) was put in a square sagger and calcinated at 750° C. in an electric furnace to obtain zinc oxide particles having a primary particle diameter of 2.21 μm. The size and form of the obtained particles were observed with a scanning electron microscope JSM-6510A (manufactured by JEOL Ltd.). The obtained electron microscope photograph is shown in FIG. 12. The results of evaluating the physical properties of the obtained particles are shown in Table 2.

Comparative Example 7

Figure 13:
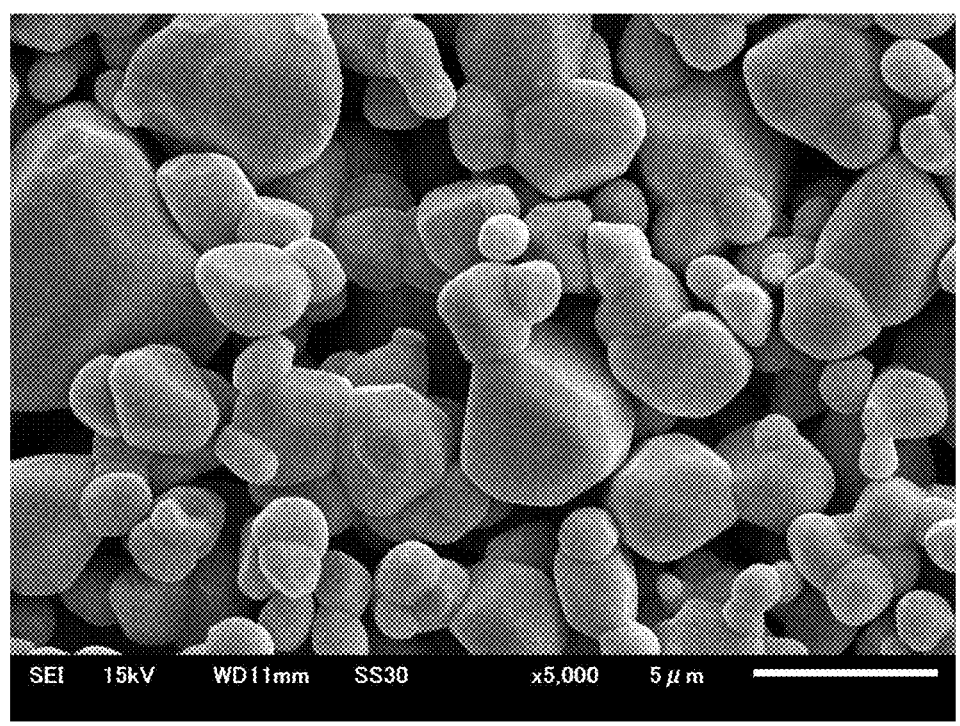
FIG. 13 is a scanning electron microscope photograph of zinc oxide particles of the present disclosure obtained in Comparative Example 7.

Raw zinc oxide (manufactured by Sakai Chemical Industry Co., Ltd., ZINC OXIDE NO. 1, particle diameter 0.6 μm) was put in a square sagger and calcinated at 800° C. in an electric furnace to obtain zinc oxide particles having a primary particle diameter of 2.93 μm. The size and form of the obtained particles were observed with a scanning electron microscope JSM-6510A (manufactured by JEOL Ltd.). The obtained electron microscope photograph is shown in FIG. 13. The results of evaluating the physical properties of the obtained particles are shown in Table 2.
(Evaluation Method)
(Composition of Obtained Particles)

Figure 2:
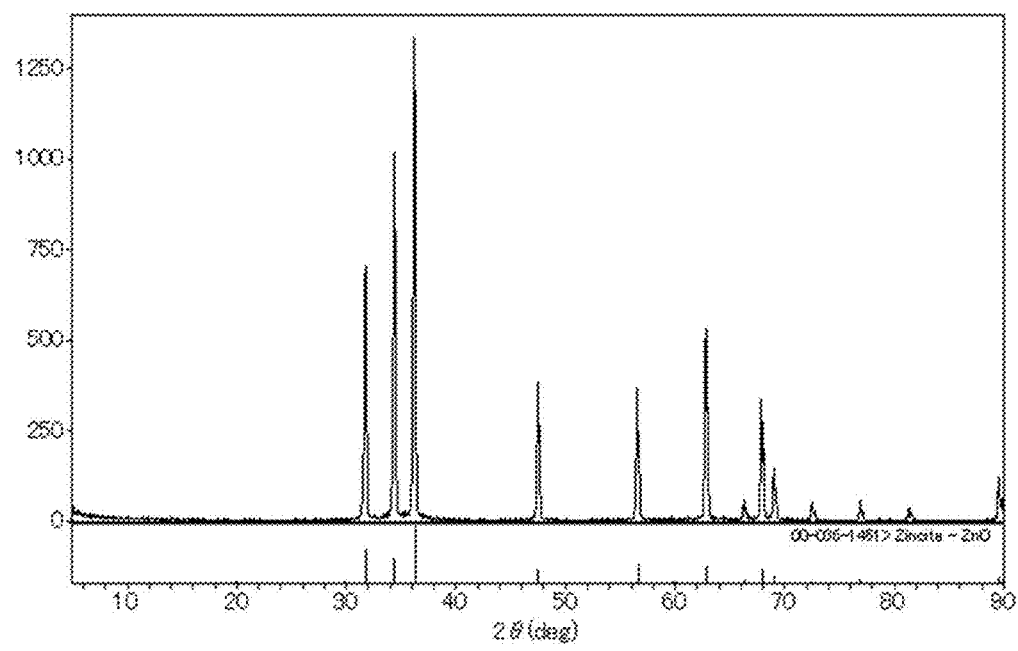
FIG. 2 is an X-ray diffraction spectrum of zinc oxide particles of the present disclosure obtained in Example 1.

The X-ray diffraction spectrum shown in FIG. 2 and the compositions of the obtained particles in Tables 1 and 2 show results of performing analysis using an X-ray diffractometer UltimaIII (manufactured by Rigaku Corporation) having an X-ray tube with copper. From these results, it is clear that zinc oxide was obtained in examples and comparative examples.
(Primary Particle Diameter)

In this specification, the primary particle diameter is a particle diameter (μm) defined by a diagonal diameter in a visual field of 2000 to 50000 magnification in a scanning electron microscope JSM-6510A (manufactured by JEOL Ltd.) photograph (a length of anyone diagonal line of three diagonal lines of the hexagonal-shaped surface of the hexagonal plate-shaped zinc oxide particle), and is obtained by measuring the diagonal diameters of 100 particles and determining an average value of a cumulative distribution thereof.
(Aspect Ratio)

In this specification, the aspect ratio of the hexagonal plate-shaped zinc oxide particles is a value determined as a ratio of L/T where L is an average value of measured particle diameters (μm) of 100 particles, the particle diameter defined by a diagonal diameter for particles in which the hexagonal plate-shaped surface of the hexagonal plate-shaped zinc oxide particle faces frontward (a length of any one diagonal line of three diagonal lines of the hexagonal plate-shaped surface of the hexagonal plate-shaped zinc oxide particle), and T is an average value of measured thicknesses (μm) (length of the shorter side of rectangle) of 100 particles for particles in which the side surface of the hexagonal plate-shaped zinc oxide particle faces frontward (particles that appear rectangular), in a visual field of 2000 to 50000 magnification in a scanning electron microscope JSM-6510A (manufactured by JEOL Ltd.) photograph.
(Dmin/Dmax)

In this specification, Dmin/Dmax was decided by the following method:

In a visual field of 2000 to 50000 magnification in a scanning electron microscope JSM-6510A (manufactured by JEOL Ltd.) photograph, three diagonal lines of the hexagonal plate-shaped surface of the hexagonal plate-shaped zinc oxide particle were measured and a length of the largest diagonal line was decided as Dmax, and a length of the smallest diagonal line was decided as Dmin. Next, a ratio between them, that is Dmin/Dmax was calculated and an average value of measured Dmin/Dmax of 100 particles was decided.
(D10, D90, and D90/D10)

In this specification, D10 and D90 were measured by using a laser diffraction/scattering particle size distribution analyzer Microtrac MT-3300 EXII (manufactured by NIKKISO CO., LTD). Each zinc oxide particle 0.1 g of examples and comparative examples was dispersed into 50 ml of sodium hexametaphosphate aqueous solution with a sodium hexametaphosphate concentration of 0.025 wt % to prepare a slurry and the obtained slurry was used for measurement. Before the measurement, the slurry was ultrasonic dispersed for two minutes by using an ultrasonic homogenizer US-600T (manufactured by NISSEI Corporation) to adjust a circulation speed at 50%, an ultrasonic output at 40 W, and an ultrasonic dispersing time at two minutes at the measurement time. The measurement was done while setting the relative refractive index of zinc oxide of example and comparative example at 1.95 and that of 0.025 wt % sodium hexametaphosphate aqueous solution at 1.333.
(MIU (Average Friction Coefficient))

MIU (average friction coefficient) in Tables 1 and 2 is determined by measuring the zinc oxide particles obtained in examples and comparative Examples with the use of KES-SE friction tester (manufactured by Kato Tech Co., Ltd.). A 25-mm-wide double-stick tape was stuck on a slide glass, and a powder was placed thereon and spread by a makeup puff. Next, MIU (average friction coefficient) of the obtained sample was measured with the use of KES-SE friction tester (manufactured by Kato Tech Co., Ltd.). The measurement was performed at a friction measurement load of 25 gf, at a surface measurement sample moving speed of 1 mm/sec, and a measurement distance range of 20 mm. As a sensor, a silicone contact piece (a friction piece of silicone rubber with irregular shape assumed as a human finger) was used.
(MMD (Mean Deviation of Friction Coefficient))

MMD (mean deviation of friction coefficient) in Tables 1 and 2 is determined by measuring the zinc oxide particles obtained in examples and comparative Examples with the use of KES-SE friction tester (manufactured by Kato Tech Co., Ltd.). A 25-mm-wide double-stick tape was stuck on a slide glass, and a powder was placed thereon and spread by a makeup puff. Next, MMD (mean deviation of friction coefficient) of the obtained sample was measured with the use of KES-SE friction tester (manufactured by Kato Tech Co., Ltd.). The measurement was performed at a friction measurement load of 25 gf, at a surface measurement sample moving speed of 1 mm/sec, and a measurement distance range of 20 mm. As a sensor, a silicone contact piece (a friction piece of silicone rubber with irregular shape assumed as a human finger) was used.

(BET Specific Surface Area)

BET specific surface area ($m^2/g$) in Tables 1 and 2 is a value measured by using a fully automatic BET specific surface area measuring device Macsorb Model HM-1200 (manufactured by Mountech Co., Ltd.).

(Spectral Reflectance at 1000 nm and Spectral Reflectance at 2000 nm)

Spectral reflectance at 1000 nm and spectral reflectance at 2000 nm in tables 1 and 2 were measured by using a spectrophotometer V-570 (manufactured by JASCO Corporation). Each zinc oxide particle 10 g of example and comparative example, 20.4 g of alkyd resin, 8.7 g of butylated melamine resin, 5.4 g of xylene, and 30 g of 1.0 mmφ glass beads were put into a 75 ml mayonnaise bottle and vibrated for 60 minutes by a paint conditioner to obtain a dispersion. The obtained dispersion was applied on a hiding-chart by using a bar coater #20, and then dried at 50° C. for 10 minutes and 110° C. for 20 minutes to obtain a test piece. The spectral reflectance at 1000 nm and 2000 nm of the obtained test piece were measured by using a spectrophotometer V-570 (manufactured by JASCO Corporation).

(Total Light Transmittance at 310 nm, Total Light Transmittance at 350 nm, and Parallel Light Transmittance at 400 nm)

Total light transmittance at 310 nm, total light reflectance at 350 nm, and parallel light transmittance at 400 nm in tables 1 and 2 were measured by using a spectrophotometer V-570 (manufactured by JASCO Corporation). Each zinc oxide particle 2 g of example and comparative example, 10 g of acryl polyol resin, 5 g of xylene, 5 g of butyl acetate and 38 g of 1.5 mmφ glass beads were put into a 75 ml mayonnaise bottle and vibrated for 90 minutes by a paint conditioner to obtain a dispersion. The obtained dispersion was applied on a slide glass by using a bar coater #6. Next, total light transmittance at 310 nm, total light transmittance at 350 nm, and parallel light transmittance at 400 nm were measured by using a spectrophotometer V-570 (manufactured by JASCO Corporation).

TABLE 1

| | | Example 1 | Example 2 | Example 3 | Example 4 | Example 5 |
|---|---|---|---|---|---|---|
| Preparing condition | Raw zinc oxide | FINEX-50 | FINEX-50 | FINEX-50 | FINEX-50 | FINEX-50 |
| | Particle diameter of raw zinc oxide (μm) | 0.02 | 0.02 | 0.02 | 0.02 | 0.02 |
| | Amount of raw zinc oxide (g) | 40 | 40 | 40 | 40 | 40 |
| | Amount of water for repulping raw zinc oxide (ml) | 430 | 430 | 430 | 430 | 430 |
| | pH adjuster for water slurry of raw zinc oxide | Sodium hydroxide aqueous solution | Sodium hydroxide aqueous solution | Sodium hydroxide aqueous solution | Sodium hydroxide aqueous solution | Sodium hydroxide aqueous solution |
| | pH of water slurry of raw zinc oxide | 13 | 13 | 14 | 10 | 13 |
| | Zinc salt aqueous solution | Zinc acetate aqueous solution | Zinc acetate aqueous solution | Zinc acetate aqueous solution | Zinc acetate aqueous solution | Zinc acetate aqueous solution |
| | Concentartion of zinc salt aqueous solution (mol/l) | 1.61 | 1.61 | 1.61 | 1.61 | 1.61 |
| | Amount of zinc salt aqueous solution (ml) | 563 | 563 | 563 | 563 | 563 |
| | Mixing time (minutes) | 120 | 120 | 120 | 120 | 120 |
| | Mixing temperature (° C.) | 15 | 30 | 30 | 15 | 15 |
| | Concentartion of zinc salt aqueous solution after mixing (mol/l) | 0.75 | 0.75 | 0.75 | 0.75 | 0.75 |
| | Aging temperature (° C.) | 95 | 95 | 95 | 95 | 95 |
| | Aging time (Hr) | 1 | 1 | 1 | 1 | 5 |
| Physical property of particle | Composition of obtained particle | Zinc oxide | Zinc oxide | Zinc oxide | Zinc oxide | Zinc oxide |
| | Shape of obtained particle | Hexagonal plate shape | Hexagonal plate shape | Hexagonal plate shape | Hexagonal plate shape | Hexagonal plate shape |
| | Primary particle diameter (μm) | 3.13 | 1.89 | 1.48 | 1.32 | 2.94 |
| | Aspect ratio | 4.0 | 4.2 | 3.6 | 4.1 | 4.2 |
| | Dmin/Dmax | 0.97 | 0.95 | 0.96 | 0.96 | 0.96 |
| | D10 (μm) | 2.27 | 1.30 | 1.30 | 0.78 | 2.04 |
| | D90 (μm) | 4.28 | 2.50 | 2.97 | 2.08 | 4.11 |
| | D90/D10 | 1.9 | 1.9 | 2.3 | 2.7 | 2.0 |
| | BET specific surface area ($m^2/g$) | 1.4 | 1.9 | 1.4 | 1.6 | 1.0 |
| | MIU (average friction coefficient) | 0.74 | 0.80 | 0.85 | 0.82 | 0.76 |
| | MMD (mean deviation of friction coefficient) | 0.013 | 0.024 | 0.019 | 0.029 | 0.014 |
| | Total light transmittance at 310 nm (%) | 78.02 | 73.04 | 73.07 | 67.04 | 72.57 |
| | Total light transmittance at 350 nm (%) | 74.72 | 68.83 | 68.55 | 62.47 | 69.27 |
| | Parallel light transmittance at 400 nm | 52.91 | 41.83 | 44.86 | 32.43 | 42.84 |
| | Spectral reflectance at 1000 nm (%) | 10.51 | 22.90 | 11.24 | 12.26 | 10.19 |
| | Spectral reflectance at 2000 nm (%) | 8.23 | 14.99 | 8.30 | 8.26 | 8.14 |

TABLE 2

|  |  | Compar. Ex. 1 | Compar. Ex. 2 | Compar. Ex. 3 | Compar. Ex. 4 |
|---|---|---|---|---|---|
| Preparing condition | Raw zinc oxide | FINEX-50 | FINEX-50 | FINEX-50 | FINEX-50 |
|  | Particle diametr of raw zinc oxide (μm) | 0.02 | 0.02 | 0.02 | 0.02 |
|  | Amount of raw zinc oxide (g) | 80 | 80 | 40 | 40 |
|  | Amount of water for repulping raw zinc oxide (ml) |  |  | 430 | 430 |
|  | pH adjuster for water slurry of raw zinc oxide |  |  | Sodium hydroxide aqueous solution |  |
|  | pH of water slurry of raw zinc oxide |  |  | 13 | 8 |
|  | Zinc salt aqueous solution | Zinc acetate aqueous solution | Zinc acetate aqueous solution | Zinc acetate aqueous solution | Zinc acetate aqueous solution |
|  | Concentartion of zinc salt aqueous solution (mol/l) | 1 | 1 | 1.61 | 1.61 |
|  | Amount of zinc salt aqueous solution (ml) | 1200 | 1200 | 563 | 563 |
|  | Mixing time (minutes) | 0.5 | 0.5 | 120 | 120 |
|  | Mixing temperature (° C.) | 25 | 25 | 40 | 30 |
|  | Concentartion of zinc salt aqueous solution after mixing (mol/l) | 1 | 1 | 0.75 | 0.75 |
|  | Aging temperature (° C.) | 100 | 100 | 95 | 95 |
|  | Aging time (Hr) | 7 | 1 | 1 | 1 |
| Physical property of particle | Composition of obtained particle | Zinc oxide | Zinc oxide | Zinc oxide | Zinc oxide |
|  | Shape of obtained particle | Hexagonal plate shape | Hexagonal plate shape | Hexagonal plate shape | Hexagonal plate shape |
|  | Primary particle diameter (μm) | 1.00 | 0.31 | 0.97 | 1.12 |
|  | Aspect ratio | 4.3 | 3.3 | 3.8 | 3.9 |
|  | Dmin/Dmax | 0.96 | 0.95 | 0.95 | 0.95 |
|  | D10 (μm) | 0.51 | 0.32 | 0.57 | 0.69 |
|  | D90 (μm) | 1.68 | 1.14 | 1.75 | 2.17 |
|  | D90/D10 | 3.3 | 3.5 | 3.1 | 3.1 |
|  | BET specific surface area ($m^2/g$) | 2.0 | 5.0 | 2.3 | 1.8 |
|  | MIU (average friction coefficient) | 0.88 | 1.07 | 0.81 | 0.89 |
|  | MMD (mean deviation of friction coefficient) | 0.033 | 0.054 | 0.037 | 0.031 |
|  | Total light transmittance at 310 nm (%) | 68.10 | 53.09 | 65.01 | 70.80 |
|  | Total light transmittance at 350 nm (%) | 63.33 | 47.24 | 62.08 | 66.11 |
|  | Parallel light transmittance at 400 nm | 29.20 | 24.84 | 26.00 | 29.45 |
|  | Spectral reflectance at 1000 nm (%) | 17.59 | 13.82 | 11.62 | 12.98 |
|  | Spectral reflectance at 2000 nm (%) | 11.24 | 7.80 | 7.57 | 9.04 |

|  |  | Compar. Ex. 5 | Compar. Ex. 6 | Compar. Ex. 7 |
|---|---|---|---|---|
| Preparing condition | Raw zinc oxide | FINEX-50 | ZINC OXIDE NO. 1 | ZINC OXIDE NO. 1 |
|  | Particle diametr of raw zinc oxide (μm) | 0.02 |  |  |
|  | Amount of raw zinc oxide (g) | 40 |  |  |
|  | Amount of water for repulping raw zinc oxide (ml) | 430 |  |  |
|  | pH adjuster for water slurry of raw zinc oxide | Acetic acid aqueous solution |  |  |
|  | pH of water slurry of raw zinc oxide | 6 |  |  |
|  | Zinc salt aqueous solution | Zinc acetate aqueous solution |  |  |
|  | Concentartion of zinc salt aqueous solution (mol/l) | 1.61 |  |  |
|  | Amount of zinc salt aqueous solution (ml) | 563 |  |  |
|  | Mixing time (minutes) | 120 |  |  |
|  | Mixing temperature (° C.) | 30 |  |  |
|  | Concentartion of zinc salt aqueous solution after mixing (mol/l) | 0.75 |  |  |
|  | Aging temperature (° C.) | 95 |  |  |
|  | Aging time (Hr) | 1 |  |  |
| Physical property of particle | Composition of obtained particle | Zinc oxide | Zinc oxide | Zinc oxide |
|  | Shape of obtained particle | Hexagonal plate shape | Indefinite shape | Indefinite shape |
|  | Primary particle diameter (μm) | 0.96 | 2.21 | 2.93 |
|  | Aspect ratio | 3.6 |  |  |
|  | Dmin/Dmax | 0.95 |  |  |
|  | D10 (μm) | 0.60 | 3.05 | 4.34 |
|  | D90 (μm) | 1.66 | 9.52 | 13.25 |
|  | D90/D10 | 2.8 | 3.1 | 3.1 |
|  | BET specific surface area ($m^2/g$) | 2.2 | 0.5 | 0.4 |
|  | MIU (average friction coefficient) | 0.89 | 0.89 | 0.88 |
|  | MMD (mean deviation of friction coefficient) | 0.036 | 0.012 | 0.014 |
|  | Total light transmittance at 310 nm (%) | 66.57 | 83.34 | 84.71 |
|  | Total light transmittance at 350 nm (%) | 62.29 | 81.02 | 81.24 |
|  | Parallel light transmittance at 400 nm | 26.78 | 61.06 | 62.14 |
|  | Spectral reflectance at 1000 nm (%) | 13.17 | 7.56 | 7.06 |
|  | Spectral reflectance at 2000 nm (%) | 9.05 | 6.05 | 6.42 |

From the results of examples 1, 2, 3, 4, and 5, it is clear that the hexagonal plate-shaped zinc oxide particles of the present disclosure have a large primary particle diameter and a sharp particle size distribution, and the values of both MIU and MMD thereof are small.

On the other hand, the particles of comparative example 4 are big particles having a primary particle diameter of 1.12 μm but D90/D10 is 3.1, that is the particle size distribution thereof is degraded, and the value of MIU is large.

The particles of comparative example 5 have a small D90/D10 of 2.8 so that it can be said that the particle size distribution is sharp. However, the primary particle diameter thereof is 0.96 μm, that is small, and both MIU and MMD thereof are large.

From the results of comparative examples 4 and 5, it is found that the values of MIU and MMD may not be reduced by the action of either the size of particle diameter or the sharpness of particle size distribution and an excellent powder touch may not be achieved.

Therefore, it is clear that the hexagonal plate-shaped zinc oxide particles of the present disclosure having small MIU and MMD and showing an excellent powder touch can be obtained by having a primary particle diameter of 1.1 μm or more and a sharp particle size distribution.

It is clear that the hexagonal plate-shaped zinc oxide particles of the present disclosure have a better infrared radiation reflective performance than conventional indefinite-shaped zinc oxide particles. Further, hexagonal plate-shaped zinc oxide particles which are out of the scope of the present disclosure absorb a light in a visible light region, but the hexagonal plate-shaped zinc oxide particles of the present disclosure do not absorb a light in a visible light region so that the particles have an excellent transparency.

INDUSTRIAL APPLICABILITY

The hexagonal plate-shaped zinc oxide particles of the present disclosure can be used for a cosmetic, an ink, a coating, and a resin composition. Further, the particles can be used as an infrared radiation reflective agent in various fields.

The invention claimed is:

1. Zinc oxide particles comprising hexagonal plate-shaped zinc oxide particles having a primary particle diameter of 1.1 μm or more and a D90/D10 of 2.8 or less in particle size distribution, wherein the percentage of the hexagonal plate-shaped zinc oxide particles is at least 81% of a total of zinc oxide particles.

2. The zinc oxide particles according to claim 1, having a MIU (average friction coefficient) of 0.87 or less and a MMD (mean deviation of friction coefficient) of 0.035 or less.

3. The zinc oxide particles according to claim 1, having the primary particle diameter of 1.3 μm or more and 30 μm or less.

4. A method for producing the zinc oxide particles according to claim 1, comprising:
   (1) preparing a water slurry of raw zinc oxide having a pH of 10 or higher;
   (2) mixing the water slurry of raw zinc oxide and a zinc salt aqueous solution at 35° C. or less; and
   (3) aging the mixed slurry of (2) with heating.

5. A cosmetic containing the zinc oxide particles according to claim 1.

6. A filler comprising the zinc oxide particles according to claim 1.

7. A resin composition comprising the zinc oxide particles according to claim 1.

8. An infrared radiation reflective material comprising the zinc oxide particles according to claim 1.

9. A coating composition comprising the zinc oxide particles according to claim 1.

\* \* \* \* \*